United States Patent
Rosen et al.

(10) Patent No.: US 12,004,797 B2
(45) Date of Patent: *Jun. 11, 2024

(54) MEDICAL SYSTEMS, METHODS, AND DEVICES FOR HYPOPIGMENTATION COOLING TREATMENTS

(71) Applicant: R2 Technologies, Inc., San Ramon, CA (US)

(72) Inventors: Jesse Rosen, Albany, CA (US); Kevin Springer, Livermore, CA (US); Kristine Tatsutani, Redwood City, CA (US); Michael O'Neil, Dublin, CA (US)

(73) Assignee: R2 Technologies, Inc., San Ramon, CA (US)

(*) Notice: Subject to any disclaimer, the term of this patent is extended or adjusted under 35 U.S.C. 154(b) by 836 days.

This patent is subject to a terminal disclaimer.

(21) Appl. No.: 16/986,780

(22) Filed: Aug. 6, 2020

(65) Prior Publication Data
US 2021/0015536 A1    Jan. 21, 2021

Related U.S. Application Data

(63) Continuation of application No. 15/257,827, filed on Sep. 6, 2016, now Pat. No. 10,765,467.
(Continued)

(51) Int. Cl.
*A61F 7/00*    (2006.01)
*A61B 18/02*    (2006.01)
(Continued)

(52) U.S. Cl.
CPC ........ *A61B 18/0206* (2013.01); *A61B 18/203* (2013.01); *A61B 2018/00458* (2013.01);
(Continued)

(58) Field of Classification Search
CPC .. A61B 2018/00476; A61B 2018/0047; A61B 2018/00452; A61B 2018/00458;
(Continued)

(56) References Cited

U.S. PATENT DOCUMENTS 3,664,344 A    5/1972 Bryne
4,206,609 A    6/1980 Durenec
(Continued)

FOREIGN PATENT DOCUMENTS

CA    2441489 A1 *    3/2005    ............. A61B 18/02
CA    2441489 A1    3/2005
(Continued)

OTHER PUBLICATIONS

Andrews, "Cryosurgery for Common Skin Conditions", American Family Physician, vol. 69 Issue 10, May 15, 2004, pp. 2365-2372.
(Continued)

*Primary Examiner* — Adam Z Minchella
(74) *Attorney, Agent, or Firm* — Kilpatrick Townsend & Stockton LLP

(57) ABSTRACT

Embodiments of the present invention generally relate to methods, devices, and systems for reducing a pigmentation of a skin of a patient. In some embodiments, freezing of the skin may be desirable to effect the hypopigmentation of the skin of the patient. Generally, embodiments may limit supercooling (or promote freezing) of the skin of the patient during a cooling treatment. In some embodiments, coupling fluids are provided to reduce a thermal contact resistance between a cooling treatment probe and the skin of the patient to improve cooling treatment. Optionally, a fluid carrier may be provided to help retain the coupling fluid at the treatment site. In some embodiments, the coupling fluid may include ice nucleating agents to promote ice crystal formation in the coupling fluid during cooling treatment. The ice crystal (Continued)

formation in the coupling fluid may progress into the skin to limit supercooling of the skin during treatment.

22 Claims, 7 Drawing Sheets

Related U.S. Application Data

(60) Provisional application No. 62/214,446, filed on Sep. 4, 2015.

(51) Int. Cl.
*A61B 18/20* (2006.01)
*A61B 18/00* (2006.01)
*A61N 7/00* (2006.01)

(52) U.S. Cl.
CPC ........... *A61B 2018/00994* (2013.01); *A61B 2018/0237* (2013.01); *A61B 2018/2023* (2017.05); *A61F 2007/0052* (2013.01); *A61N 7/00* (2013.01)

(58) Field of Classification Search
CPC .......... A61B 2018/00464; A61B 18/02; A61B 18/0206; A61B 2018/00005; A61B 2018/00011; A61F 2007/0052
See application file for complete search history.

(56) References Cited

U.S. PATENT DOCUMENTS

| | | |
|---|---|---|
| 5,596,875 A | 1/1997 | Berry et al. |
| 5,654,279 A | 8/1997 | Rubinsky et al. |
| 5,759,182 A | 6/1998 | Varney et al. |
| 5,848,981 A | 12/1998 | Herbranson |
| 5,901,707 A | 5/1999 | Goncalves |
| 6,017,337 A | 1/2000 | Pira |
| 6,430,956 B1 | 8/2002 | Haas et al. |
| 6,503,246 B1 | 1/2003 | Har-Shai et al. |
| 6,629,417 B2 | 10/2003 | Haas et al. |
| 6,981,970 B2 | 1/2006 | Karni |
| 7,367,341 B2 | 5/2008 | Anderson et al. |
| 7,630,774 B2 | 12/2009 | Karni et al. |
| 7,751,452 B2 | 7/2010 | Vogler |
| 7,850,683 B2 | 12/2010 | Elkins et al. |
| 8,150,532 B2 | 4/2012 | Karni et al. |
| 8,435,194 B2 | 5/2013 | Dverin et al. |
| 8,579,835 B2 | 11/2013 | Britva et al. |
| 8,950,406 B2 | 2/2015 | Karni et al. |
| 9,522,031 B2 | 12/2016 | Anderson et al. |
| 2003/0004556 A1* | 1/2003 | McDaniel ............... A61K 8/361 607/88 |
| 2003/0100936 A1 | 5/2003 | Altshuler et al. |
| 2003/0220674 A1 | 11/2003 | Anderson et al. |
| 2004/0167592 A1 | 8/2004 | Grove et al. |
| 2004/0261782 A1* | 12/2004 | Furumichi ............... B01D 9/005 126/263.01 |
| 2005/0222565 A1 | 10/2005 | Manstein |
| 2006/0058238 A1 | 3/2006 | Laurent-Applegate et al. |
| 2006/0189976 A1 | 8/2006 | Karni et al. |
| 2007/0088386 A1 | 4/2007 | Babaev et al. |
| 2007/0129714 A1 | 6/2007 | Elkins et al. |
| 2007/0135876 A1 | 6/2007 | Weber |
| 2007/0185527 A1 | 8/2007 | Babaev |
| 2008/0039747 A1 | 2/2008 | Baerwalde et al. |
| 2008/0077211 A1 | 3/2008 | Levinson et al. |
| 2008/0119839 A1 | 5/2008 | Vancelette |
| 2008/0183164 A1 | 7/2008 | Elkins et al. |
| 2008/0183167 A1 | 7/2008 | Britva et al. |
| 2008/0255644 A1 | 10/2008 | Carson |
| 2008/0287943 A1 | 11/2008 | Weber et al. |
| 2009/0012585 A1 | 1/2009 | Karni et al. |
| 2009/0171424 A1 | 7/2009 | Britva et al. |
| 2009/0281537 A1 | 11/2009 | Britva et al. |
| 2009/0299361 A1 | 12/2009 | Flyash et al. |
| 2010/0036295 A1 | 2/2010 | Altshuler et al. |
| 2010/0114007 A1 | 5/2010 | Fischer et al. |
| 2011/0313411 A1* | 12/2011 | Anderson ............ A61B 18/0218 606/20 |
| 2012/0041525 A1 | 2/2012 | Karni |
| 2012/0071794 A1 | 3/2012 | Karni |
| 2012/0089211 A1 | 4/2012 | Curtis et al. |
| 2012/0123319 A1 | 5/2012 | Britva et al. |
| 2012/0330194 A1 | 12/2012 | Britva et al. |
| 2014/0007895 A1 | 1/2014 | Britva et al. |
| 2014/0135662 A1 | 5/2014 | Britva et al. |
| 2014/0200506 A1 | 7/2014 | Zemel et al. |
| 2014/0303696 A1* | 10/2014 | Anderson ................ A61F 7/02 607/104 |
| 2014/0303697 A1 | 10/2014 | Anderson et al. |
| 2015/0045857 A1 | 2/2015 | Britva et al. |
| 2015/0080991 A1 | 3/2015 | Britva et al. |
| 2015/0216719 A1* | 8/2015 | DeBenedictis ......... A61B 18/02 607/108 |
| 2015/0216720 A1 | 8/2015 | DeBenedictis et al. |
| 2015/0223975 A1* | 8/2015 | Anderson ............... A61B 18/02 607/104 |
| 2015/0303696 A1 | 10/2015 | Nethery |
| 2016/0157915 A1 | 6/2016 | Anderson et al. |
| 2017/0065323 A1 | 3/2017 | Rosen et al. |

FOREIGN PATENT DOCUMENTS

| | | |
|---|---|---|
| CN | 1214624 A | 4/1999 |
| CN | 1658804 A | 8/2005 |
| CN | 102143724 A | 8/2011 |
| CN | 108135644 A | 6/2018 |
| DE | 9217897 U1 | 11/1993 |
| EP | 1797847 A1 | 6/2007 |
| EP | 2201917 A1 | 6/2010 |
| EP | 2272455 A1 | 1/2011 |
| EP | 3344176 | 7/2018 |
| GB | 2286660 A | 8/1995 |
| JP | 4133822 A | 5/1992 |
| JP | 10052475 A | 2/1998 |
| JP | 2005237908 A | 9/2005 |
| JP | 2008537504 A | 9/2008 |
| KR | 200431404 Y1 | 11/2006 |
| KR | 100802155 B1 | 2/2008 |
| RU | 2074680 C1 | 3/1997 |
| WO | 2003078596 A2 | 9/2003 |
| WO | 2005096979 A1 | 10/2005 |
| WO | 2006066226 A1 | 6/2006 |
| WO | 2006127467 A2 | 11/2006 |
| WO | 2007064718 A2 | 6/2007 |
| WO | 2008055243 A2 | 5/2008 |
| WO | 2008083305 A2 | 7/2008 |
| WO | 2008091983 A2 | 7/2008 |
| WO | 2009146053 A1 | 12/2009 |
| WO | 2010017477 A2 | 2/2010 |
| WO | 2013075006 A1 | 5/2013 |
| WO | 2013075016 A1 | 5/2013 |
| WO | 2017041022 A1 | 3/2017 |

OTHER PUBLICATIONS

Gage et al., "Critical Temperature for Skin Necrosis in Experimental Cryosurgery", Cryobiology 19, 1982, 273-282.

Gage et al., "Sensitivity of Pigmented Mucosa and Skin to Freezing Injury", Cryobilogy 16, 1979, 348-361.

Har-Shai, et al., "Effect of skin surface temperature on skin pigmentation during contact and intralesional cryosurgery of hypertrophic scars and Kleoids", Journal of the European Academy of Dermatology and Venereology, vol. 21, Issue 2, Feb. 2007, pp. 191-198.

Thai et al., "Cryosurgery of Benign Skin Lesions", Australasian Journal of Dermatology 40, 1999, 175-186.

Yeh, "Cryosurgical Treatment of Melanin-Pigmented Gingiva", Mackay Memorial Hospital, Jun. 1998, 1-4.

(56) References Cited

OTHER PUBLICATIONS

Zachariassen, et al., "Ice Nucleation and Antinucleation in Nature", Crybiology, vol. 41, Issue 4, Dec. 2000, pp. 257-279.

\* cited by examiner

MEDICAL SYSTEMS, METHODS, AND DEVICES FOR HYPOPIGMENTATION COOLING TREATMENTS

CROSS REFERENCE TO RELATED APPLICATIONS

The present application is a continuation of U.S. patent application Ser. No. 15/257,827 filed Sep. 6, 2016, entitled "MEDICAL SYSTEMS, METHODS, AND DEVICES FOR HYPOPIGMENTATION COOLING TREATMENTS," which claims the benefit of and priority to U.S. Provisional Patent Application 62/214,446 filed Sep. 4, 2015, entitled "MEDICAL SYSTEMS, METHODS, AND DEVICES FOR LIMITING SUPERCOOLING OF SKIN DURING HYPOPIGMENTATION COOLING TREATMENTS," the entire contents of each which are incorporated herein in their entirety for all purposes.

BACKGROUND

Embodiments of the present invention generally relate to methods, devices, and systems for reducing a pigmentation of a skin of a patient. More specifically, embodiments generally relate to methods, devices, and systems to increase the chance of freezing (water phase transition) in the skin.

Controlled freezing of biological tissue, such as skin tissue, can produce various effects. Certain tissue freezing procedures and devices, such as conventional cryoprobes, can cause severe freezing of tissue and generate cellular damage. It has been observed that moderate degrees of freezing can produce particular effects, such as affecting the expression of skin pigmentation.

There is a demand for cosmetic products that can lighten the appearance of skin or otherwise controllably affect skin pigmentation. For example, it may be desirable to lighten the overall complexion or color of a region of skin to alter the general appearance for cosmetic reasons. Also, lightening of particular hyperpigmented regions of skin, such as large freckles, 'café au lait' spots, melasma, or dark circles under the eyes that may result from excessive local amounts of pigment in the skin, may also be desirable for cosmetic reasons. Hyperpigmentation can result from a variety of factors such as UV exposure, aging, stress, trauma, inflammation, etc. Such factors can lead to an excess production of melanin, or melanogenesis, in the skin by melanocytes, which can lead to formation of hyperpigmented areas. Such hyperpigmented areas are typically associated with excess melanin within the epidermis; however, they can also result from excess melanin deposited within the dermis.

Hypopigmentation of skin tissue has been observed as a side effect in response to temporary cooling or freezing of the tissue, such as may occur during cryosurgery procedures. Loss of pigmentation following skin cooling or freezing may result from decreased melanin production, decreased melanosome production, destruction of melanocytes, or inhibited transfer of melanosome into the keratinocytes in the lower region of the epidermal layer. The resultant hypopigmentation may be long-lasting or permanent. However, it has also been observed that some of these freezing procedures can generate regions of hyperpigmentation of skin tissue. The level of increase or decrease in pigmentation may be dependent upon certain aspects of the cooling or freezing conditions, including the temperature of the cooling treatment, and the length of time the tissue is exposed to freezing conditions.

While some hypopigmentation treatments, devices, and systems have been previously developed, further improvements may be desired. Toward this end, it may be desirable to improve the consistency of skin freezing and the consistency of a duration of skin freezing. Such improvements may be desirable to improve overall hypopigmentation consistency. For example, with some cooling treatments, the skin may sometimes freeze toward the beginning of the cooling treatment, or may sometimes cool to a temperature below the freezing point (e.g., 0 to $-5°$ C.) for a period and then freeze thereafter. With some cooling treatments, the skin may become supercooled (cooled to a temperature below the freezing point) and may not freeze at all during the cooling treatment. Such variability in the skin freezing (i.e., the formation of water ice in the skin) may result in less than optimal treatment.

In light of the above, it may be desirable to improve the consistency or repeatability of hypopigmentation treatments, in particular hypopigmentation treatments provided via skin freezing. At least some embodiments of the present invention may provide additional control over the occurrence of freezing and may limit supercooling or otherwise promote freezing of the skin during a cooling treatment.

SUMMARY OF THE INVENTION

The present invention generally relates to improved medical devices, systems, and methods, with exemplary embodiments providing improved cooling treatment probes and cooling treatment methods and systems. In some embodiments, freezing of the skin may be desirable to effect the hypopigmentation of the skin of the patient. Generally, embodiments may limit supercooling or otherwise promote freezing of the skin of the patient during a cooling treatment. In some embodiments, coupling fluids are provided to reduce a thermal contact resistance between a cooling treatment probe and the skin of the patient to improve cooling treatment. Optionally, a fluid carrier may be provided to help retain the coupling fluid at the treatment site. In some embodiments, the coupling fluid may include ice nucleating agents to promote ice crystal formation in the coupling fluid during cooling treatment. The ice crystal formation in the coupling fluid may progress into the skin to limit supercooling or otherwise promote freezing of the skin during treatment.

Some aspects of the present invention may provide a method of altering a pigmentation and/or melanin of a skin of a patient. For example, some embodiments may lighten the skin of a patient (i.e., hypopigmentation). The method may include applying a coupling fluid to a treatment area on the skin of the patient. The coupling fluid may include an ice nucleating agent configured to promote ice formation in the coupling fluid. A cooling treatment may be applied to the treatment area with the applied coupling fluid present. The cooling treatment and ice nucleating agent may promote ice crystal formation in the coupling fluid. The ice crystal formation in the coupling fluid may propagate into the skin of the patient and limit supercooling or otherwise promote freezing of the skin of the patient during the cooling treatment.

The ice nucleating agent may be organic or inorganic. Optionally, the ice nucleating agents are inorganic materials such as soot, dust, fine particulates (microparticles, nanoparticles, or the like), or silver iodide, silver oxide, or alumina crystals. Other ice nucleating materials that can be added to the coupling fluid may be organic substances such as proteins, lipoproteins, bacteria or fungi. Long chain aliphatic alcohols and amino acids, such as l-aspartic acid can also be added to the coupling fluid (e.g., water). In some embodiments, the coupling fluid may have a freezing point near 0° C., to help reduce or limit the chance of supercooling in the tissue.

In some embodiments, the method may further include abrading or piercing the treatment area prior to applying the cooling treatment. The abrading or piercing of the treatment area may be performed by abrading or piercing the treatment area using a microderm abrasion roller or a laser. The abrasion or piercing of the treatment area may facilitate ice crystal formation or propagation into the skin of the patient.

Optionally, the coupling fluid may be applied to the treatment area on the skin of the patient by applying a fluid carrier to the treatment area of the skin. The fluid carrier may be pre-saturated with a fluid and may be configured to retain the coupling fluid at the treatment area. In some embodiments, the fluid carrier has a uniform thickness. The fluid carrier may be a woven or nonwoven fabric material. In some embodiments, the coupling fluid may be an aqueous fluid including a thickening agent that increases viscosity of the aqueous fluid. The thickening agent may help retain the coupling fluid at the treatment site.

The cooling treatment may be applied by contacting a treatment surface of a cooling probe with the coupling fluid at the treatment site. Optionally, the cooling probe may include a vibrator for triggering or otherwise facilitate ice formation by applying vibrations to the treatment area of the skin. The vibrator may be an acoustic transducer, an ultrasound transducer, or a motor with an eccentric weight for example. In some embodiments, the cooling treatment may be applied by contacting a treatment surface of a cooling probe with the coupling fluid at the treatment site where the treatment surface of the cooling probe comprises a textured or rough surface (e.g., knurled surface or the like) having recessed areas configured to retain ice crystals. The surface may have a roughness between 32-256 µin (micro inches). In some embodiments, the surface may alternatively have a roughness of 1000-2000 µm or greater. Surface roughness or Ra (average surface roughness) is a typical part call-out and can be measured by standard metrology techniques including with a profilometer which has a stylus that is dragged along the surface and measures local height variations of the surface.

In further aspects of the present invention, a method of altering pigmentation of skin of a patient may be provided that may include applying a fluid carrier to a treatment area on the skin of the patient and infusing the fluid carrier with a coupling fluid. Thereafter a cooling treatment may be applied to the treatment area of the skin to promote ice crystal formation in the coupling fluid retained by the fluid carrier. The ice crystal formation in the coupling fluid may propagate into the skin of the patient and may limit supercooling or otherwise promote freezing of the skin of the patient during the cooling treatment. Optionally, the skin may be abraded or pierced prior to applying the cooling treatment. The fluid carrier may have a uniform thickness. The fluid carrier may be a fabric material (e.g., gauze or the like).

In yet another aspect of the invention, a method of altering pigmentation of a target area of a skin of a patient may be provided that may include abrading or piercing the epidermis layer of a skin defining a target area and applying a coupling fluid to the target area on the skin of the patient. A cooling treatment may be applied to the treatment area with the applied coupling fluid present. The cooling treatment may promote ice crystal formation in the coupling fluid and the ice crystal formation in the coupling fluid may propagate into the skin of the patient and limit supercooling or otherwise promote freezing of the skin of the patient during the cooling treatment.

In further aspects, a method of altering pigmentation of a skin of a patient may be provided. The method may include pre-treating a contact surface of a cooling treatment probe by misting a liquid on the contact surface. The contact surface of the cooling treatment probe may be at a temperature below a freezing point of the liquid. Accordingly, the misted liquid may form ice crystals on the contact surface of the cooling treatment probe. A fluid carrier may be applied to a treatment area on the skin of the patient. Thereafter, the pretreated contact surface of the cooling treatment probe with the ice crystals may be contacted with the coupling fluid at the treatment site. The cooling treatment probe in addition to the ice crystals formed by the pretreatment may promote ice crystal formation in the coupling fluid. The ice crystal formation in the coupling fluid may propagate into the skin of the patient and may limit supercooling or otherwise promote freezing of the skin of the patient during the cooling treatment.

Additional embodiments of the present invention may provide a system for altering pigmentation of a skin of a patient. The system may include a cooling treatment probe. The cooling treatment probe may include a contact surface for contacting a treatment area of the skin of the patient with a coupling fluid present at the treatment area. The contact surface may have a textured surface having recessed areas configured to promote ice crystal formation in the coupling fluid during a cooling treatment. The ice crystal formation in the coupling fluid may be configured to propagate into the skin of the patient to limit supercooling or otherwise promote freezing of the skin of the patient during cooling treatment.

In some embodiments, the cooling treatment probe may include a vibrator for vibrating the contact surface of the cooling treatment probe to trigger or otherwise facilitate ice formation. The vibrator may be an ultrasound transducer or the like.

The system may include the coupling fluid. The coupling fluid may include an ice nucleating agent for application to the treatment area of the skin of the patient. The ice nucleating agent may be a bacteria, a fungi, soot, dust, a protein, lipoprotein, or a long-chain aliphatic alcohol or amino acid or the like. A fluid carrier may be provided for application to the treatment area and for retaining coupling fluid at the treatment area. The fluid carrier may have a uniform thickness. The fluid carrier may be a fabric material (e.g., gauze, cloth, or the like).

In additional aspects, a system for altering pigmentation of skin of a patient may be provided that includes a fluid carrier configured to be applied to a treatment area of the skin. The fluid carrier may be configured to be infused with a coupling fluid and to retain the coupling fluid at the treatment area of the skin. A cooling treatment probe may be provided that includes a contact surface for contacting the fluid carrier. The contact surface of the cooling treatment probe configured to promote ice crystal formation in the coupling fluid retained in the fluid carrier. Optionally, the fluid carrier may have a uniform thickness and may be made of a fabric material.

In further aspects, a system for altering pigmentation of a skin of a patient may be provided that includes a cooling treatment probe comprising a contact surface for contacting a treatment area of the skin of the patient with a coupling fluid present at the treatment area. A vibrator may be provided for vibrating the contact surface of the cooling treatment probe to trigger or otherwise facilitate ice formation in the coupling fluid during a cooling treatment. The ice crystal formation in the coupling fluid may be configured to propagate into the skin of the patient to limit supercooling or otherwise promote freezing of the skin of the patient during cooling treatment. In at least some embodiments, the vibrator may be an ultrasound transducer.

Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The invention will be better understood upon reading the following description and examining the figures which accompany it. These figures are provided by way of illustration only and are in no way limiting on the invention.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE INVENTION

Figure 1:
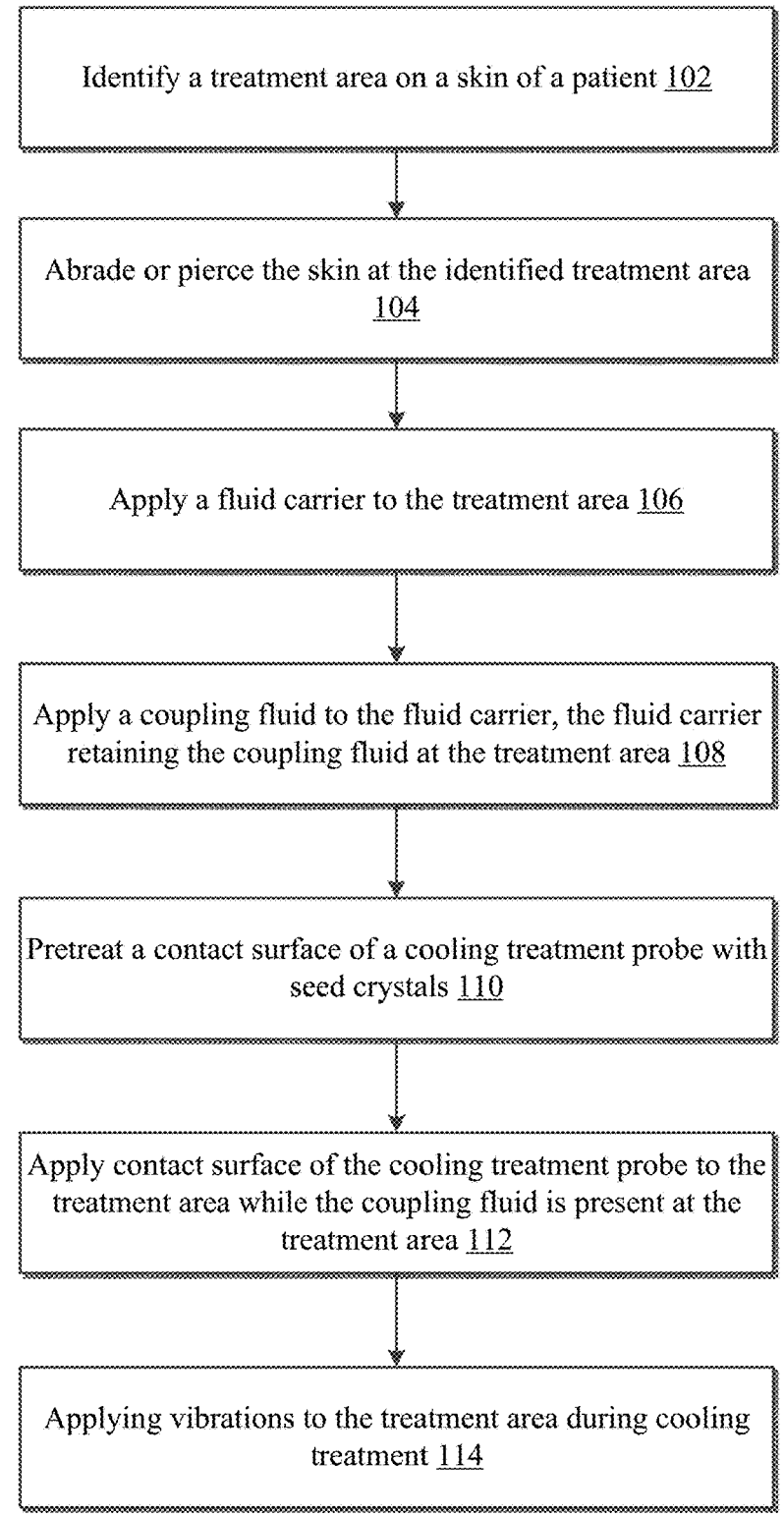
FIG. 1 illustrates an exemplary method according to some embodiments of the present invention.

As set forth above, some embodiments of the present invention may be directed to techniques to affect melanocytes of a patient. For example, some embodiments may be directed to methods and systems for reducing skin pigmentation by cooling the skin of a patient. In some embodiments it may be beneficial to freeze the skin. Additionally, it may be advantageous to freeze the skin in a more controllable and consistent manner. The freezing event, although it may not be required, has been shown to have an effect on both the desired outcome of reduced pigmentation, but also the short term side effects of epidermal necrosis and in some cases prolonged erythema and hyperpigmentation. In previous studies, the timing of skin freezing has been found to be inconsistent. Different results (time to freezing, or lack of freezing) have been seen when replicates of the same treatment parameters are performed. Accordingly, some embodiments of the present invention provide increased control over the occurrence of freezing in the skin of a patient and may limit supercooling or otherwise promote freezing in the skin. Methods and systems described herein may thus increase the chance, predictability, and/or consistency of freezing in the skin of a patient (e.g., repeatable freezing at certain temperatures and/or cooling rates) and may thereby provide additional control over a duration of skin freezing during treatment. Some embodiments may be directed to limiting supercooling or otherwise promote freezing of the skin of a patient during a cooling treatment.

Supercooling of the skin may be cooling of the skin below the water freezing point without solidification or crystallization of water in the skin.

A number of cooling systems have been developed for lightening the pigmentation of skin (see e.g., U.S. Patent Publication 2011/0313411; U.S. Patent Publication 2014/0303696; U.S. Patent Publication 2014/0303697). In general, the systems provide a cooling contact surface configured to contact and freeze skin tissue (typically the superficial layer of skin down to the dermal/epidermal junction). The freezing of the skin tissue may decrease melanin production, decrease melanosome production, destroy meloncytes, and/or inhibit transfer of melanosome into keratinocytes in the lower region of the epidermal layer, thereby leading to skin lightening (i.e., hypopigmentation) for a period of time or permanently.

Some treatments may use relatively modest skin cooling to temperatures in the range of 0° C. to −20° C. over fairly short times frames, e.g., as short as 15 seconds or less and up to 2 minutes or more. In some embodiments, skin cooling may be performed by controlling the temperature of an aluminum plate (e.g. cooler) and applying the cooler directly to the skin—thereby cooling the skin through thermal conduction from the skin to the cooler.

It has been observed that in some instances, cooling treatments (e.g., at −5 to −10deg. C) may lead to local supercooling of the skin, where the tissue does not freeze. Supercooling of the tissue alone may be insufficient to result in hypopigmentation or may extend the length of treatment. Accordingly, embodiments of the present invention help reduce or limit the occurrence of tissue supercooling during a cooling treatment for hypopigmentation.

In some embodiments, a coupling fluid may be provided between the contact surface of the treatment system and the skin. The coupling fluid may be water or may be another fluid that freezes near 0 deg. C. The fluid may include ice nucleating agents (INAs) to reduce supercooling and to facilitate freezing of the tissue. The ice nucleating agents may be organic (e.g., proteins, lipoproteins, bacteria, fungi, etc.) or inorganic (e.g., dust, soot, Silver Iodine, etc.). In some embodiments, the coupling fluid may include long-chain aliphatic alcohols or amino acids (e.g., L-aspartic acid or the like). In some aspects, the skin may be pierced or abraded prior to or during the cooling treatment. The piercing or abrasion may create small holes in the epidermis and may facilitate ice crystal propagation from the coupling fluid into the superficial layers of the skin. In some embodiments, the fluid includes a thickening agent to increase the viscosity such that a uniform layer may be consistently applied. In other embodiments, the fluid is loaded in a carrier, such as a woven or nonwoven cloth so as to retain a uniform layer of fluid at the interface. Fluid-loading may occur at the time of treatment or carriers may be loaded and prepackaged for use.

FIG. 1 illustrates an exemplary treatment method 100 for altering melanin content or melanocytes in a skin of a patient according to some embodiments of the present invention. At 102, a treatment area of a skin of a patient may be identified. At 104, the treatment area may be abraded or pierced. At 106, a fluid carrier may be applied to the treatment area. At 108, a coupling fluid may be applied to the fluid carrier and the fluid carrier may retain at least a portion of the coupling fluid at the treatment area 108. At 110, a contact surface of a cooling treatment probe may be pre-treated with seed crystals. At 112, the contact surface of the cooling treatment probe may be contacted with the treatment area while the coupling fluid is present at the treatment area to cool and/or freeze the skin at the treatment area. At 114, vibrations may be applied to the treatment area during the cooling treatment to promote ice crystal formation in the coupling fluid and/or the skin of the patient.

In some embodiments, the treatment area of a skin of a patient may be a pigmentation blemish of the skin. The pigmentation blemish may include hyperpigmentation, freckles, birthmarks, liver spots, age spots, café au lait spots, and pigmentation blemishes such as melasma. In some embodiments, a pigmentation blemish may be a superficial blemish or a blemish in the epidermis, e.g., liver spots, birthmarks, freckles, or the like. In further embodiments, the pigmentation blemish may be or include a blemish in the dermis, e.g., deep pigmentation blemishes such as melasma or the like. Optionally, the treatment area may be an area of skin where the patient would prefer overall lightening of a complexion of the skin.

In some embodiments, a skin surface of the identified treatment area may be may be abraded or pierced 104. During a cooling treatment, ice may start to form at the interface of a cooling treatment probe. In order to freeze the skin, the ice may then need to propagate into the skin from the cooling probe interface. The epidermis, however, is generally impervious to water, although there are specialized areas such as sweat glands that are specifically designed to control the flow of moisture across this barrier. It may be however that ice propagation is limited across the epidermis as the skin is cooled which could result in supercooling in the tissue. To limit this, small holes can be made in the epidermis to allow ice to freely propagate across this barrier.

Holes can be initiated by abrasions with a rough cloth, brush, luffa, or sponge, with a dermabrasion or microdermabrasion roller or system, with a laser, electroporation or with a number of additional techniques or combinations thereof. For example, in some embodiments a dermaroller with 0.5 mm needles may be used to manually pierce the dermis. Optionally, a dermapen may be used with a depth setting of about 0.5 mm which punches rather than rolls holes into the dermis. In some embodiments, the epidermis may be pierced. In some embodiments dermis is minimally pierced. Optionally, in some embodiments, various combinations of abrasion or piercing of the skin may be performed. While abrading the skin or piercing the skin may be desired in some embodiments, it should be understood that these steps may be absent or even avoided in other embodiments of the present invention.

In some embodiments, freezing can be triggered more reliably by specifying and maintaining a fluid at an interface between a cooling treatment applicator and the skin. For example, in some embodiments, water may be the coupling fluid that can be used to reduce the thermal contact resistance between a cooling probe applicator and the skin and thereby improve cooling. In some embodiments, the coupling fluid may be a solution, a suspension, an emulsion, a colloid or the like. For example, in some embodiments, the coupling fluid may contain a thickening agent to increase viscosity. The thickening agent may be helpful to maintain the coupling fluid at the treatment site.

Some coupling fluids such as water however, may experience supercooling below its typical freezing point under certain conditions. Accordingly, in some embodiments, substances can therefore be mixed with the coupling fluid to limit or reduce the chance of supercooling or otherwise promote freezing. Some such substances that may limit the occurrence of supercooling or otherwise promote freezing include inorganic materials such as soot, dust, fine particulates, or silver iodide crystals. Other materials that can be added to a coupling fluid are organic substances such as proteins, lipoproteins, bacteria or fungi. For example, in some embodiments *Pseudomonas syringae* may be included and act as an ice nucleating agent. Optionally, long chain aliphatic alcohols and amino acids, such as l-aspartic acid can also be added to the water, or other fluid, with a freezing point near 0° C., to reduce the chance of supercooling in the tissue. In some embodiments, it may be preferable if the additives do not significantly decrease the freezing point of the coupling fluid. Water for example has a freezing point generally of 0° C. which is very near that of the skin tissue.

Freezing can additionally be encouraged by applying a carrier at the interface. The fluid carrier may help retain the coupling fluid at the treatment area. The fluid carrier may be a piece of gauze or another woven or non-woven material that is saturated with the coupling fluid. The carrier may occupy some volume, but may allow the free transfer of coupling fluid across it. This carrier may help ensure that a desired volume of water or other fluid is present at the interface which facilitates freezing of the skin. In some embodiments, it may be preferable if the fluid carrier is of uniform thickness. Optionally, the fluid carrier may be combined with a treatment probe. In many embodiments, however, the fluid carrier and fluid may be individually packaged and provided as disposable parts. In some embodiments, a fluid carrier may be applied to a pre-cooled applicator to temporarily attach the fluid carrier to the applicator surface through at least partial freezing of the coupling fluid. It should be understood that the use of a fluid carrier is optional. In some embodiments of the present invention, controlled and predictable freezing of the skin of the patient may be provided through the utilization of a coupling fluid alone, for example.

Figure 2A:
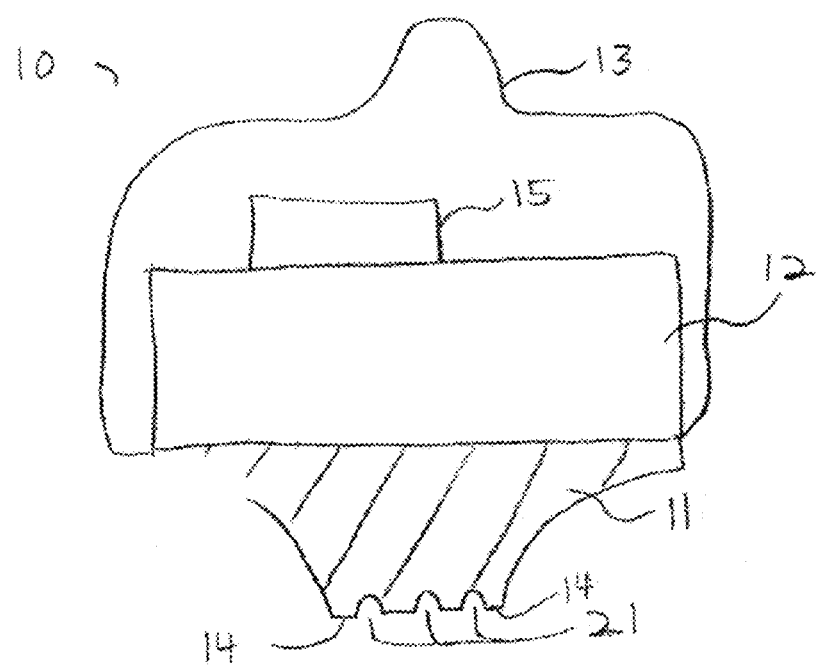
FIG. 2A is an exemplary cross-sectional side view of an exemplary apparatus that can be used to produce hypopigmentation in a skin tissue according to exemplary embodiments of the present invention.

The cooling probe may optionally be the cooling treatment apparatuses described in U.S. Patent Publication 2011/0313411, U.S. Patent Publication 2014/0303696, U.S. Patent Publication 2014/0303697, or U.S. Patent Publication 2015/0223975, the disclosures of which are incorporated herein by reference in their entirety. For example, FIG. 2A illustrates a side cross-sectional view of an exemplary apparatus 10 that can be used to produce a hypopigmentation in a skin tissue according to some embodiments of the present invention. The exemplary apparatus 10 can include a contact element 11 provided in a thermal communication with a cooling arrangement 12. In certain exemplary embodiments, the contact element 11 and the cooling arrangement 12 can be formed at least in part from a single material. A control arrangement 15 can optionally be provided and used to control certain aspects of the cooling arrangement 12, e.g., temperature, timed shutoff, etc. The cooling arrangement 12, control arrangement 15, and/or contact element 11 can optionally be provided within or affixed to a housing or handpiece 13, as shown in FIG. 2A, e.g., to facilitate handling and positioning of the apparatus 10. The exemplary apparatus 10 shown in FIG. 2A is not necessarily drawn to scale. For example, the relative dimensions of the cooling arrangement 12 and contact element 11 are not limited to the proportions illustrated in the FIG. 2A. In further exemplary embodiments of the present disclosure, the contact element 11 can be larger or smaller in width or cross-sectional area as compared to the dimensions of the cooling arrangement 12.

The contact element 11 can include a distal (contact) surface 14 that is configured to contact a skin surface. The distal surface 14 can be substantially flat. In further exemplary embodiments of the present disclosure, the distal surface 14 can be convex or concave to better match the local shape of skin tissue being treated and/or to provide good thermal contact with the skin surface when the apparatus 10 is placed on the area of the skin to be treated. In still further exemplary embodiments of the present disclosure, the contact element 11 can be detachable from the cooling arrangement 12, e.g., so that a plurality of contact elements 11 having different sizes, shapes, and/or surface features as described herein can be used with a single cooling element 12.

The distal contact surface 14 can have a large width or diameter configured to contact the surface of a region of skin, e.g., a diameter or width that is greater than about 3-10 cm, or greater than about 5 cm, to facilitate treatment of large areas of skin. In further embodiments, the width of the distal surface 14 can be small, e.g., on the order of 1-2 cm or less, which may facilitate improved temperature control and/or treatment of particular features on the skin.

The contact element 11 can be formed from a metal or a metal alloy, or another material having a high thermal effusivity, e.g., such that values of these thermophysical properties are greater than the corresponding values for skin tissue. The thermal effusivity c is equal to the square root of the product of a material's thermal conductivity and its volumetric heat capacity. The thermal effusivity is a measure of the ability of a material to exchange heat with its surroundings and to maintain a consistent temperature as it does so. For example, the interface temperature $T_i$ where two semi-infinite materials at temperature $T_1$ and $T_2$, respectively, are brought into contact will depend on their relative effusivities, $\varepsilon_1$ and $\varepsilon_2$, as $T_i=T_1+(T_2-T_1)*[\varepsilon_2/(\varepsilon_2+\varepsilon_1)]$. Accordingly, e.g., with $\varepsilon_2 \gg \varepsilon_1$, the interface temperature where the two materials are in contacts will remain close to $T_2$ as heat flows from one to the other. In this manner, the surface of a first material will be cooled down close to the temperature of a second material having a much higher thermal effusivity when the second material is brought into contact with the first material.

For example, the contact element 11, at least in part or wholly, can be made of brass, copper, silver, aluminum, an aluminum alloy, steel, graphite, diamond, diamond-like carbon, other materials which are used in conventional contact cryoprobes, or combinations thereof. For example, the contact element 11 can be formed, wholly or at least in part, from materials having a much higher thermal conductivity than the skin tissue, and can be used to facilitate an extraction of heat from the portion of the tissue contacted by the distal surface 14 of the contact element 11. Further, materials having a much higher thermal effusivity than the skin tissue, e.g. at least about 10 times the thermal effusivity of skin, can be more readily maintained at a cold temperature. Such high-effusivity materials thereby may extract heat more effectively from the portion of tissue contacted by the contact element 11 than materials having lower thermal effusivities, and facilitate a better control of the tissue temperature at a contact interface.

In certain exemplary embodiments of the present disclosure, the distal contact surface 14 of the contact element 11 can be smaller in area than the proximal end of the contact element 11 that contacts the cooling arrangement 12. Such geometry can provide certain advantages. For example, the narrower or tapered distal end of the contact element 11 can facilitate a more precise placement of the distal surface 14 on a particular location of the skin surface to be cooled, e.g., while reducing visual obstruction by the housing 13. Further, the relatively larger proximal end of the contact element 11 can provide a larger area that can be directly cooled by the cooling arrangement 12 to facilitate increased extraction of heat from the smaller distal contact surface 14. In certain embodiments, the area of the proximal end of the contact arrangement distal contact surface 14 can be at least twice as large as the area of the distal contact surface 14, e.g., 3-5 times as large.

The distal surface 14 of the contact element 11 can be provided with a plurality of dimples 21, e.g., indentations or pockets formed in the contact surface 14 of the contact element 11, as shown in the cross-sectional side view of FIG. 2A. Such dimples 21 can be substantially round and have a diameter or width that is between about 0.3 mm and about 3 mm, or between about 0.5 mm and 2 mm, or optionally about 1 mm. The depth of the dimples can be between about 0.3 mm and about 2 mm, or between about 0.5 mm and about 1.5 mm, or optionally about 1 mm. The edges of the distal surface 14 can be rounded or beveled, as shown in FIG. 2A, which can facilitate continuous contact of the distal surface 14 with the skin surface while avoiding contact with any sharp or abrupt edges or corners when the apparatus 10 is placed against the skin surface for treatment.

Figure 2B:
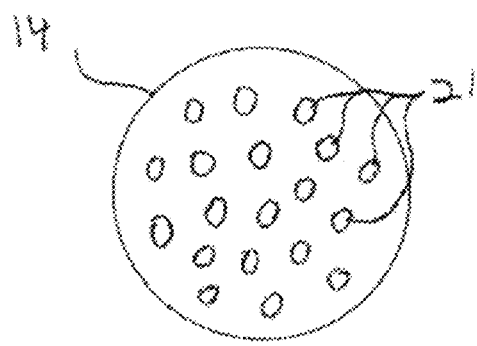
FIG. 2B is a bottom view of an exemplary configuration of the contact element of the apparatus of FIG. 2A according to some embodiments.

An exemplary end view of the contact surface 14 with dimples 21 is shown in FIG. 2B. An area fraction of the dimples 21 on the contact surface 14 can be e.g., between about 0.05 and about 0.50, or optionally between about 0.10 and about 0.30, or about 0.20. Such exemplary ranges and values of fractional area coverage can provides a sufficient area of direct skin contact by the contact surface 14 while also providing sufficient areal density of dimples 21 to improve local cooling and/or freezing efficacy to generate hypopigmentation effects.

Although the size and depth of the exemplary dimples shown in FIGS. 2A and 2B are substantially uniform, individual dimple sizes and/or depths associated with a single contact element 11 can vary within the ranges described herein in further embodiments of the disclosure.

Figure 2C:
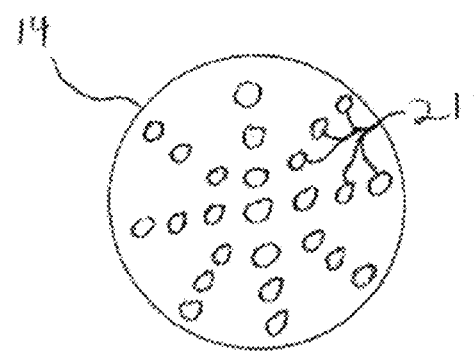
FIG. 2C is a bottom view of an exemplary configuration of the contact element of the apparatus of FIG. 2A according to some embodiments.
Figure 2D:
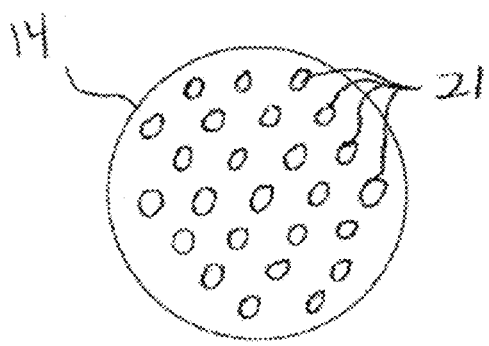
FIG. 2D is a bottom view of an exemplary configuration of the contact element of the apparatus of FIG. 2A according to some embodiments.

The exemplary arrangement of the dimples 21 on the contact surface 14 can be substantially random, as shown in FIG. 2B. In a further exemplary embodiment of the present disclosure, shown in FIG. 2C, the dimples 21 can be provided in a radial arrangement. Such exemplary arrangement/configuration can yield a lower density of dimples 21 (e.g., a wider average spacing between adjacent dimples 21), which may lead to a reduced effect of the dimples 21 near the perimeter of the contact surface 14. In a still further embodiment, the dimples 21 can be provided in a regular array, e.g., a hexagonal array as shown in FIG. 2D, or a square array.

Figure 2E:
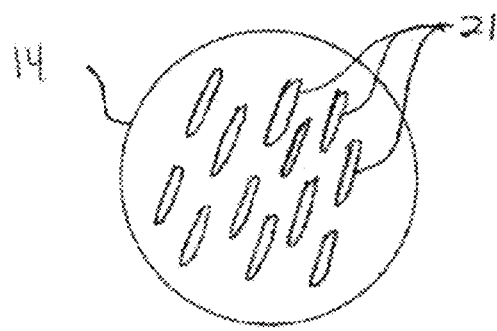
FIG. 2E is a bottom view of an exemplary configuration of the contact element of the apparatus of FIG. 2A according to some embodiments.

In further exemplary embodiments of the present disclosure, the dimples 21 can have an elongated shape, as shown in the exemplary configuration in FIG. 2E. Such elongate dimples 21 can have a smaller dimension (e.g., width) that is between about 0.5 mm and about 3 mm, or optionally about 1 mm. A longer dimension (e.g., length) of such elongate dimples 21 can be greater than the width, e.g., twice the width or longer. For example, the exemplary dimples 21 shown in FIG. 2E have a length that is about five times greater than the width. Other exemplary length-to-width ratios can be provided in further exemplary embodiments of the present disclosure. The depth of the elongate dimples 21 can be between about 0.3 mm and about 2 mm, or between about 0.5 mm and about 1.5 mm, or optionally about 1 mm. The edges of the distal surface 14 can be rounded and/or beveled where these dimples 21 meet the contact surface 14, as shown in FIG. 2A.

Figure 2F:
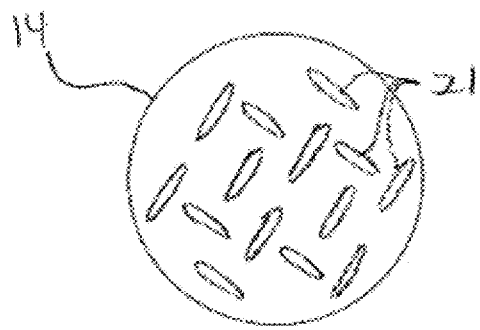
FIG. 2F is a bottom view of an exemplary configuration of the contact element of the apparatus of FIG. 2A according to some embodiments.
Figure 2G:
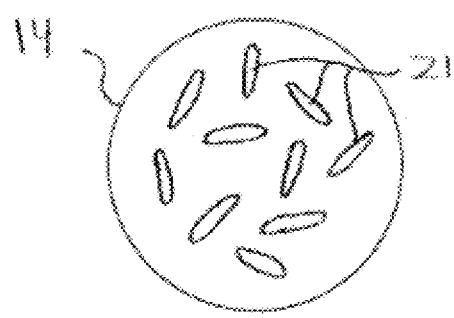
FIG. 2G is a bottom view of an exemplary configuration of the contact element of the apparatus of FIG. 2A according to some embodiments.

The long axes or dimensions of the exemplary elongate dimples 21 shown in FIG. 2E can be substantially parallel to one another. In a still further exemplary embodiment of the present disclosure, the long axes of some elongate dimples 21 can be substantially perpendicular to other ones, e.g., as shown in FIG. 2F. In still further exemplary embodiments of the present disclosure, the long axes of the elongate dimples 21 can be provided at various angles to one another on the contact surface 14. The elongate dimples 21 can be provided in a regular array or pattern, as shown in FIGS. 2E and 2F. Alternatively or in addition, the elongate dimples 21 can be provided in a non-uniform or random arrangement, as shown, e.g., in FIG. 2G.

Figure 2H:
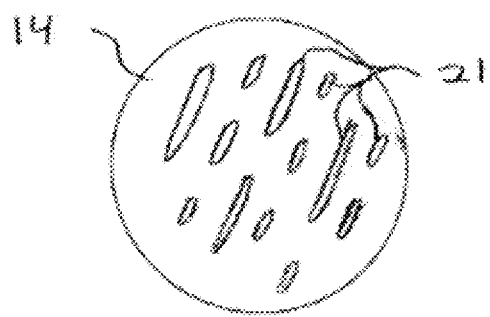
FIG. 2H is a bottom view of an exemplary configuration of the contact element of the apparatus of FIG. 2A according to some embodiments.
Figure 2I:
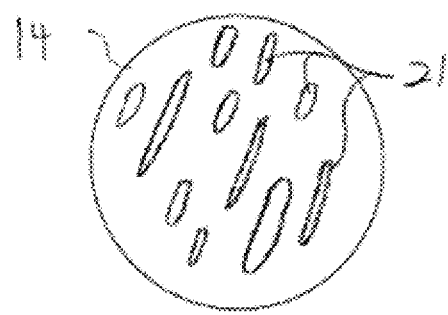
FIG. 2I is a bottom view of an exemplary configuration of the contact element of the apparatus of FIG. 2A according to some embodiments.
Figure 2J:
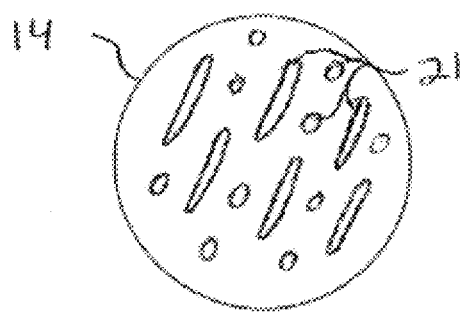
FIG. 2J is a bottom view of an exemplary configuration of the contact element of the apparatus of FIG. 2A according to some embodiments.
Figure 2K:
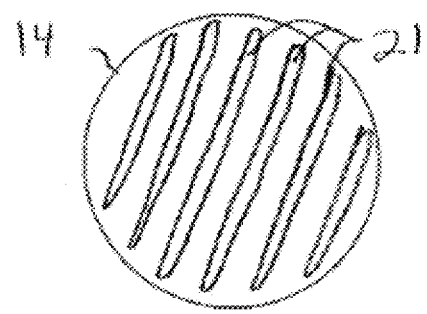
FIG. 2K is a bottom view of an exemplary configuration of the contact element of the apparatus of FIG. 2A according to some embodiments.

In further exemplary embodiments of the present disclosure, individual ones of the dimples 21 provided on a single distal contact surface 14 can have different sizes, shapes, and/or orientations. For example, different ones of the elongate dimples 21 can have the same width (small dimension) and different aspect ratios (e.g., ratios of length to width) as shown, e.g., in FIG. 2H. In further exemplary embodiments of the present disclosure, different ones of the dimples 21 can have different widths and/or different lengths from one another as shown, e.g., in FIG. 2I. In still further exemplary embodiments of the present disclosure, the contact surface 14 can include both round and elongate dimples 21 as shown, e.g., in FIG. 2J. In general, it can be preferable that the width (or diameter) and depth of the various dimples 21 are within the size ranges described herein. In yet another exemplary embodiment of the present disclosure, elongate dimples 21 can be provided as a plurality of substantially parallel grooves, as shown, e.g., in FIG. 2K. The ends of such dimples 21 can lie within the perimeter of the contact surface 14 as shown in the exemplary configuration of FIG. 2K. Alternatively, the elongate dimples 21 can extend through the perimeter of the contact surface 21, such that at least some of the dimples 21 form continuous grooves that span the full length of the contact surface 14.

The interior surface of a dimple 21 can be rounded, cylindrical, or square in profile, or have another shape. For example, the interior surface of a round dimple 21 can be cylindrical or can have the shape of a portion of a sphere or an ellipsoid. The interior surface of an elongate dimple 21 can have a shape that is rounded, such as a portion of a circular or ellipsoidal cylinder, or it may be provided with internal corners, e.g., as a squared off channel or the like.

In general, a nearest distance between adjacent ones of the dimples 21 at the contact surface can be at least as large as the width of the dimples 21. This exemplary distance between adjacent dimples 21 can be greater than their width, e.g., as shown in FIGS. 2B-2K. Such separation distances can facilitate sufficient heat extraction from the vicinity of each dimple 21 and provide a sufficient area of the contact surface 14 between dimples 21 so the contact surface 14 can be placed comfortably against the skin surface.

The shape of the exemplary contact surface 14 shown in FIGS. 2B-2K is substantially round. In a further exemplary embodiment of the present disclosure, the contact surface 14 can be provided with a shape that is substantially square, rectangular, or hexagonal. Such shapes can facilitate treatment of larger areas of skin by successively contacting adjacent areas thereof with the contact surface 14 while reducing or avoiding significant overlap in treated areas. In further embodiments, the contact surface 14 can have still different shapes.

The aspect ratio of the contact surface shape can be varied in different exemplary embodiments. For example, a square, rectangular or hexagonal shape of the contact surface 14 can facilitate uniform coverage of a larger area of skin tissue by sequential placement of the apparatus 10 on adjacent regions of skin tissue, such that substantially all of the desired treatment area of skin has been cooled by the apparatus 10 with little or no overlap of such treatment regions. Other exemplary plate shapes and/or sizes can also be provided, e.g., to conform to particular regions of skin and/or to conform to a shape of a particular skin feature to be treated such as, e.g., an age spot or the like.

One or more of any of the exemplary dimple shapes, dimensions, dimple patterns, contact surface sizes and shapes, etc., or combinations thereof, can be used with any of the exemplary embodiments and features of the present disclosure. For example, a single contact surface 14 can include a plurality of dimple shapes (e.g. round, elongated, etc.), spatial arrangements, etc., and certain various ones of such dimples 21 provided on a single contact surface 14 can have one or more characteristic diameters, widths and/or depths, as described herein.

While not illustrated, it should be understood that in other embodiments, the distal surface of the contact element 11 may be a smooth surface (e.g., not dimpled and without protrusions). A smooth distal surface of contact element 11 may or may not be roughened. In some embodiments, a smooth distal surface may be textured or roughened in order to help capture or retain ice crystals during treatment— including cleaning and/or pre-treatment (described in further detail below).

In some embodiments of the present invention, the contact surface of the cooling treatment probes may be pre-treated with seed crystals. As set forth above, the occurrence of supercooling may be limited or reduced by presenting an ice nucleating agent which serves as a nucleation source for the coupling fluid at or just below its freezing point. In some embodiments, the seed crystal may be frozen water, or ice (or frozen coupling fluid). It has been observed that when the applicator surface is cleaned with alcohol just prior to cooling skin, supercooling is more likely. It is speculated that the alcohol slows or eliminates ice nucleation on the applicator surface and thereby reduces or eliminates available ice crystals on the applicator surface. Accordingly, in some embodiments, the contact surface of a cooling treatment probe may be sprayed with a mist of water or other liquid, which will freeze on the contact surface prior to the treatment to ensure that the applicator has ice crystals. In some embodiments, it may be helpful to allow the applicator surface to dwell at a temperature below freezing for a period of time prior to the treatment to ensure water from the air freezes on the contact surface. In some embodiments, a dwell time may be 0.5-3 minutes, preferably 1-2 minutes in typical environments. Dwell times may be dependent, in-part, on ambient humidity where longer dwell times may be preferable in drier environments.

In further embodiments, the contact surface may be textured to include grooves or depressions to retain ice crystals even after being cleaned with alcohol or other cleaners. Optionally, the contact surface may include a rough texture that may harbor ice crystals or that may help seed ice crystal formation. In some embodiments, the contact surface may have an Ra of 64 μin or greater (e.g., 64-128 μin or more), and possibly 1000-2000 μin further embodiments. In certain embodiments, the contact surface may be knurled. The knurled surface may have grooves that are 0.1-0.8 mm deep. In addition these recessed areas prevent the ice from melting when first applied to warm skin.

The contact surface of the cooling treatment probe may be contacted with the treatment area while the coupling fluid is present at the treatment area 112. The cooling treatment may promote ice crystal formation in the coupling fluid. The ice crystal formation in the coupling fluid may then propagate into the skin of the patient to freeze the skin. As set forth above, the skin abrasion or piercing or the like, the coupling fluid with or without ice nucleating agents, the use of fluid carriers, the pretreatment of a contact surface of a cooling treatment probe, and/or the utilization of a treatment probe with a textured or roughened contact surface may limit supercooling or otherwise promote freezing of the skin of the patient during the cooling treatment and may thereby provide more consistent skin freezing treatments.

While the treatment apparatuses described in U.S. Patent Publication 2011/0313411, U.S. Patent Publication 2014/0303696, U.S. Patent Publication 2014/0303697, or U.S. Patent Publication 2015/0223975 may be used with embodiments of the present invention, in further embodiments of the invention, the cooling treatment probe may include one or more vibrators for vibrating a contact surface of the cooling treatment probe. The vibrations or other kinds of mechanical perturbations generated by the cooling treatment probe may help trigger or otherwise facilitate or promote ice nucleation in the fluid medium and/or the skin of the patient. In some embodiments, acoustic transducers or ultrasound may be incorporated in the system design to help control the nucleation event. Accordingly in some embodiments, the vibrator may include one or more acoustic or ultrasound transducers (piezo elements or the like). The ultrasound transducer may deliver acoustic energy in the 20-100 kHz range. Optionally the vibrator may be an electrical motor with an unbalanced mass on its drive shaft. While a cooling treatment probe with an integrated vibrator or ultrasound transducer may be beneficial in some embodiments, it should be understood that cooling treatment probes without vibrators may be used in other embodiments.

While method 100 is described above with specificity, it should be understood that some steps are optional and may be excluded in other embodiments of the invention. For example, while coupling fluids with or without ice nucleating agents and/or thickening agents may be desired in some embodiments, other embodiments of the cooling treatment may be performed without the coupling fluids. Additionally, the order of the steps presented above is by no way limiting. Other embodiments of the treatment method may perform steps in different orders and combinations as desired.

FIGS. 3-6 illustrate a treatment of a treatment area 200 of a skin 202 of a patient. The treatment area 200 may be a freckle, birthmark, liver spot, age spot, café au lait spot, or pigmentation blemishes such as melasma or the like. The skin 202 includes a dermal layer 204 and an epidermal layer 206. In some embodiments, the methods and systems described herein provide freezing of the skin tissue down to the dermal/epidermal junction 208. The freezing of the skin tissue may decrease melanosome production, destroy melanocytes, and/or inhibit the transfer of melanosome into keratinocytes in the lower region of the epidermal layer, thereby leading to skin lightening.

Figure 3:
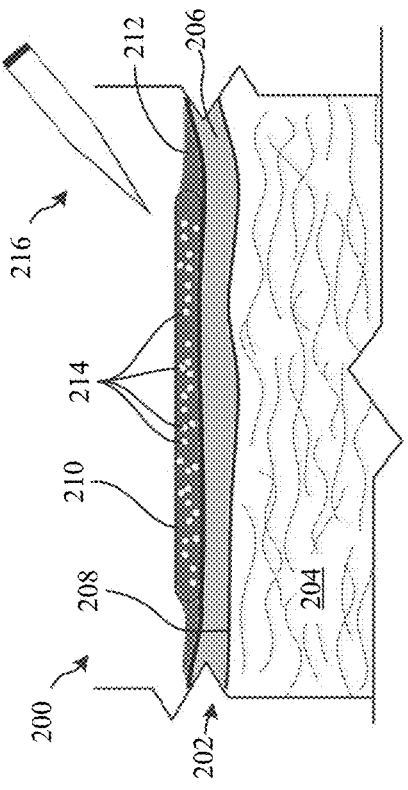
FIG. 3 illustrates the application of a fluid carrier to a treatment area of a skin of a patient according to some embodiments of the present invention.

FIG. 3 illustrates the application of a fluid carrier 210 to a skin 202 of a patient according to some embodiments of the present invention. The fluid carrier 210 may be a piece of gauze or another woven or non-woven material as described above. The fluid carrier 210 may help retain an amount of coupling fluid at the treatment area 200.

Figure 4:
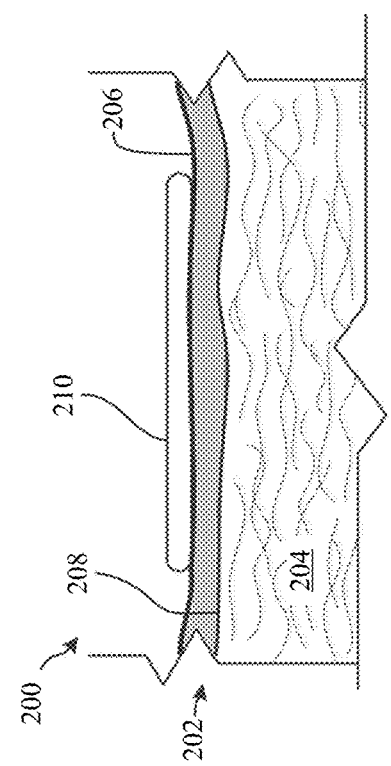
FIG. 4 illustrates the application of a coupling fluid having ice nucleating agents or thickening agents to a treatment area according to some embodiments of the present invention.

FIG. 4 illustrates the application of a coupling fluid 212 having ice nucleating agents or thickening agents 214 according to some embodiments of the present invention. Optionally, the coupling fluid 212 may be applied to the area using a syringe or infusion cannula 216 in some embodiments. The coupling fluid may be water or another fluid. The ice nucleating agents may be organic (e.g., bacteria, fungi, proteins, etc.) or inorganic (e.g., dust, soot, silver iodine, etc.). Thickening agents may be used (e.g., starch or the like) to increase the viscosity of the coupling fluid 212 so as to limit the amount of runoff of the coupling fluid 212 from the treatment area 200.

Figure 5:
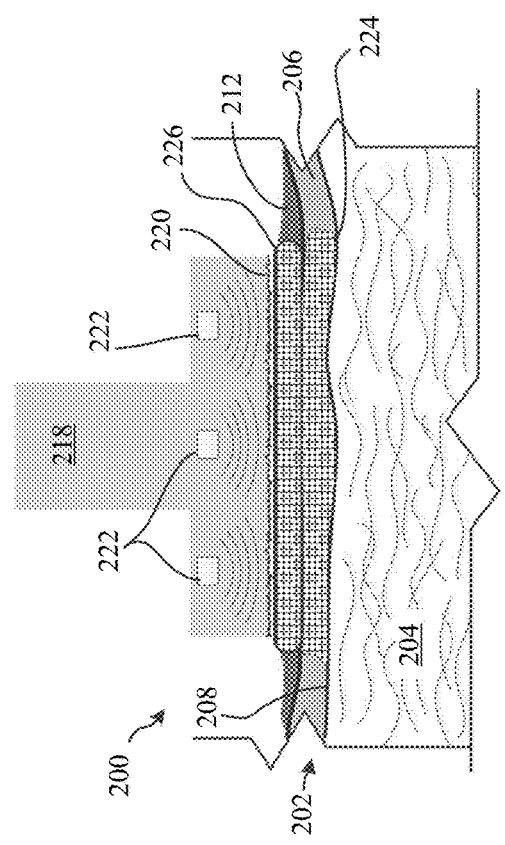
FIG. 5 illustrates a cooling treatment applied by an exemplary cooling treatment probe to freeze at least a portion of the treatment area of the skin according to some embodiments of the present invention.

FIG. 5 illustrates a cooling treatment applied by an exemplary cooling treatment probe 218 to freeze at least a portion of the skin 202 according to some embodiments of the present invention. The cooling treatment probe 218 includes a cooling contact surface 220. The cooling contact surface 220 may be cooled to a treatment temperature (e.g., −20 to 0° C.; −10 to −2° C.). Optionally, the cooling contact surface 220 may be pretreated by being cooled to the treatment temperature for a threshold duration of time (e.g., 20 seconds-2 minutes) prior to treatment such that moisture in the air forms seed crystals on the contact surface 220 prior to application of the contact surface 220 with the treatment area 200. In low humidity situations, the cooling contact surface 220 may be pretreated by misting or otherwise applying a fluid onto the contact surface 220 so that the applied on fluid forms ice crystals on the contact surface 220. In some embodiments, the cooling contact surface 220 may have a textured or roughened surface. The textured or roughened surface of contact surface 220 may limit the amount of supercooling of the skin 202 of the patient. In some embodiments, the cooling treatment probe 218 may further include one or more vibrators 222. The one or more vibrators 222 may be ultrasound transducers or the like and may vibrate or mechanically perturb the contact surface 220 of the cooling treatment probe 218 to limit supercooling or otherwise promote freezing of the skin 202 of the patient. In some embodiments, the contact surface 220 promotes ice crystal formation 224 in skin 202 of the patient with the assistance of the textured surface of the contact surface 220, the coupling fluid 212, the ice nucleating agents 214, and/or the vibrators 222. For example, the contact surface 220 may promote ice crystal formation 226 in the coupling fluid 212 (and in fluid carrier 210). Ice crystal formation 226 in the coupling fluid 212 may then progress through the skin 202 to promote ice crystal formation 224 in the epidermal layer 206.

Figure 6:
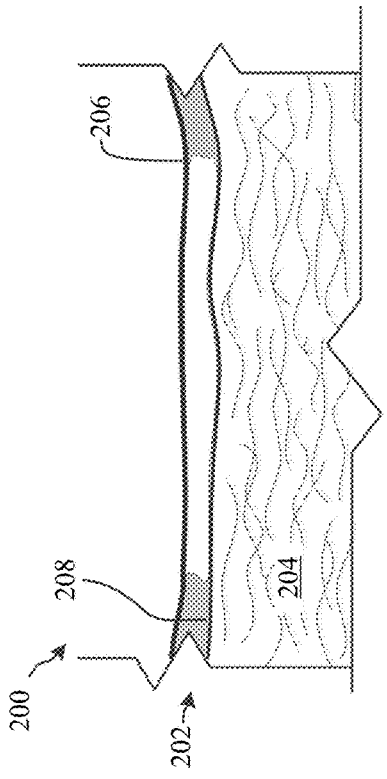
FIG. 6 illustrates a reduction in melanin and/or melanocytes in the top layer of the skin according to some embodiments of the present invention.

FIG. 6 illustrates a reduction in melanin in the epidermal layer 206 of the skin 202 after ice crystal formation 224 in the epidermal layer 206 according to some embodiments of the present invention.

FIGS. 7-10 illustrate a treatment of a treatment area 300 of a skin 302 of a patient. The treatment area 300 may be a freckle, birthmark, liver spot, age spot, café au lait spot, or pigmentation blemishes such as melasma or the like. The skin 302 includes a dermal layer 304 and an epidermal layer 306. In some embodiments, the methods and systems described herein provide freezing of the skin tissue down to the dermal/epidermal junction 308. The freezing of the skin tissue may decrease melanin production, decrease melanosome production, destroy melanocytes, and/or inhibit the transfer of melanosome into keratinocytes in the lower region of the epidermal layer, thereby leading to skin lightening.

Figure 7:
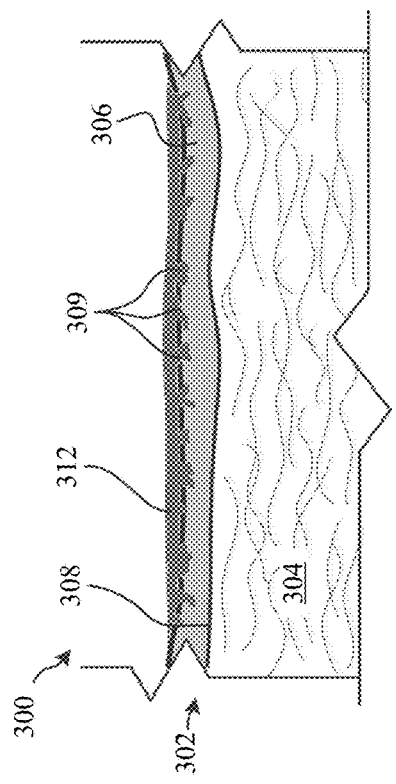
FIG. 7 illustrates exemplary abrasion or piercing of the target area of the skin of the patient prior to treatment according to some embodiments of the present invention.
Figure 8:
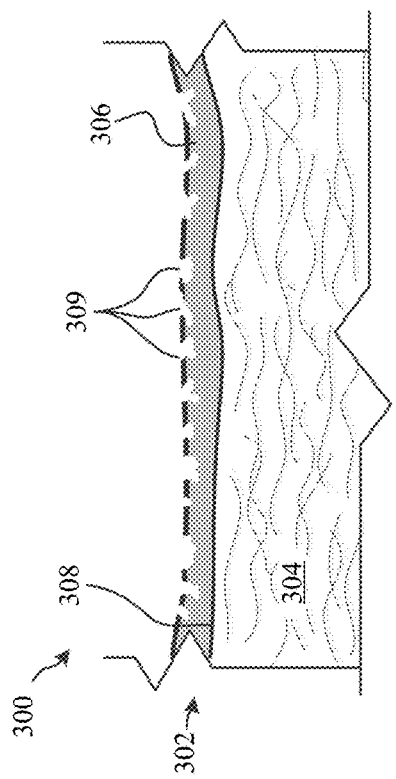
FIG. 8 illustrates the application of a coupling fluid (with or without ice nucleating agents and/or thickening agents) to the treatment area of the skin according to some embodiments of the present invention.

FIG. 7 illustrates exemplary abrasion or piercing of the skin 302 of the patient prior to treatment according to some embodiments of the present invention. Holes 309 can be introduced by abrasions with a rough cloth or brush, with a microderm abrasion roller or system, with a laser, or with a number of additional techniques (e.g., sandpaper or the like). FIG. 8 illustrates the application of a coupling fluid 312 to the treatment area 300 of the skin 302 according to some embodiments of the present invention. While not essential, in some embodiments, ice nucleating agents or thickening agents may be added to the coupling fluid 312. As illustrated, the coupling fluid 312 may penetrate a depth into the epidermal layer 306 of the skin 302 of the patient with the abrasion/piercing of the skin 302 prior to treatment.

Figure 9:
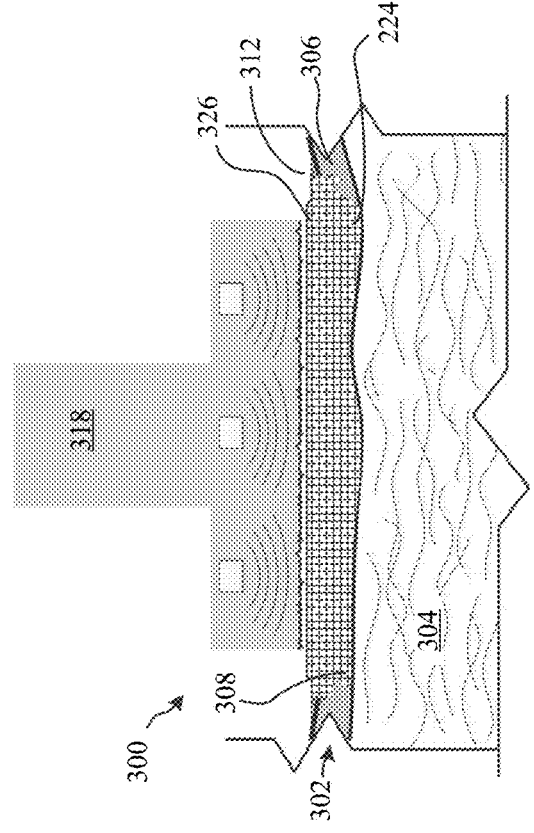
FIG. 9 illustrates a cooling treatment applied by an exemplary cooling treatment probe to freeze at least a portion of the treatment area of the skin of the patient according to some embodiments of the present invention.

FIG. 9 illustrates a cooling treatment applied by an exemplary cooling treatment probe 318 to freeze at least a portion of the skin 302 according to some embodiments of the present invention. Cooling treatment probe 318 may be similar to cooling treatment probe 218. While a textured contact surface and/or vibrators may be beneficial for promoting ice formation in the skin 302 of the patient, other cooling treatment probes may be used, such as those described in U.S. Patent Publication 2011/0313411, U.S. Patent Publication 2014/0303696, U.S. Patent Publication 2014/0303697, or U.S. Patent Publication 2015/0223975, previously incorporated by reference.

Figure 10:
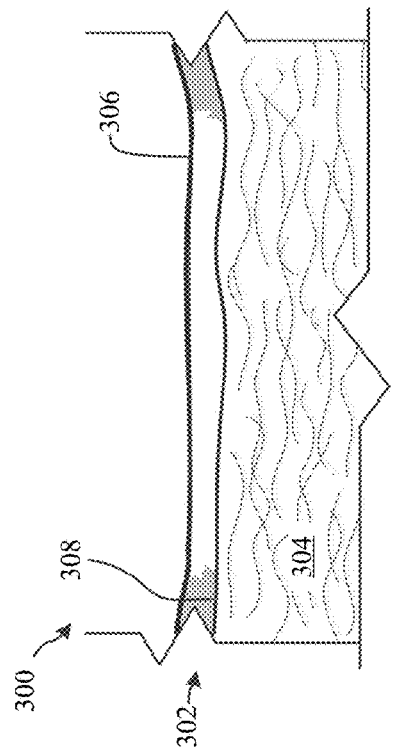
FIG. 10 illustrates a reduction in melanin and/or melanocytes in the top layer of the skin according to some embodiments of the present invention.

The cooling treatment probe 318 may promote ice crystal formation 326 in the coupling fluid 312. Thereafter, the ice crystal formation 326 may progress through the holes 309 created in the skin 302 and into the epidermal layer 306. The ice crystal formation in the epidermal layer may lead to a reduction in melanin and/or melanocytes in the epidermal layer 306 of the skin of the patient as illustrated in FIG. 10.

Figure 11:
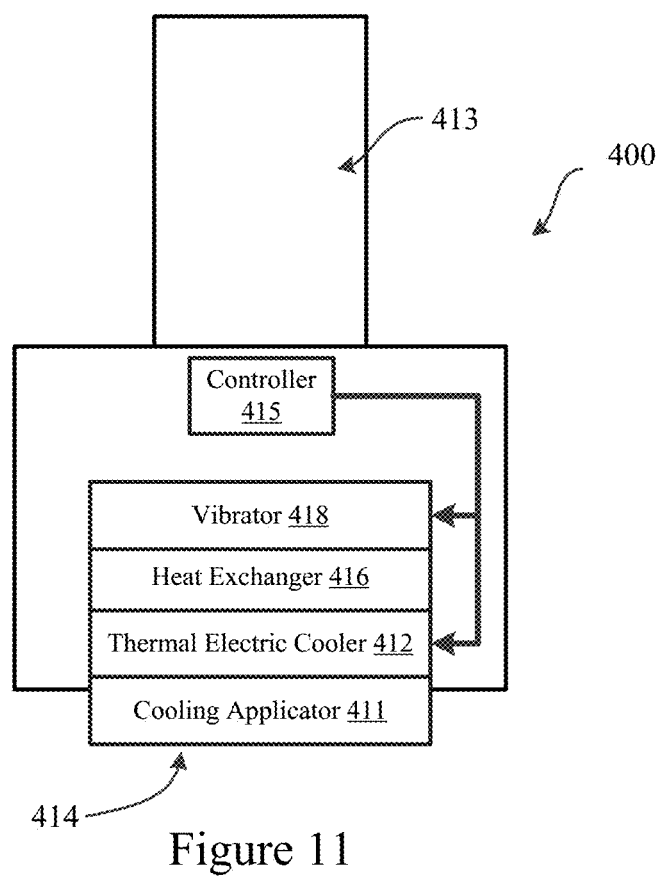
FIG. 11 illustrates an cross-sectional side view of an exemplary cooling treatment apparatus that can be used to produce hypopigmentation in a skin tissue according to some embodiments of the present invention.

FIG. 11 illustrates an exemplary cross-sectional side view of an exemplary cooling treatment apparatus 400 that can be used to produce hypopigmentation in a skin tissue according to some embodiments of the present invention. The exemplary apparatus 400 can include a cooling applicator 411 provided in a thermal communication with a thermoelectric cooler 412. A heat exchanger 416 may be thermally coupled with the thermoelectric cooler 412 on a side opposite from the cooling applicator 411. In certain exemplary embodiments, the cooling applicator 411 and the cooling arrangement 412 can be formed at least in part from a single material. As discussed above, a vibrator 418 (e.g., acoustic transducer, ultrasound transducer, or the like) may be provided. In some embodiments, the ultrasound transducer 418 may be coupled with a distal side of the heat exchanger 416 so that the ultrasound transducer 418 is on the opposite side of the heat exchanger 416 relative to the thermal electric cooler. A controller 415 can be provided and used to control certain aspects of the thermoelectric cooler 412, e.g., temperature, etc. Additionally, the controller 415 may be coupled with the ultrasound transducer 418 to control the delivery (e.g., timing, power, frequency, etc.) of the ultrasound from the ultrasound transducer 418. The thermoelectric cooler 412, controller 415, ultrasound transducer 418, and/or cooling applicator 411 can optionally be provided within or affixed to a housing or handpiece 413, as shown in FIG. 11, e.g., to facilitate handling and positioning of the apparatus 400. The exemplary apparatus 400 shown in FIG. 11 is not necessarily drawn to scale.

For example, the relative dimensions of the thermoelectric cooler 412 and cooling applicator 411 are not limited to the proportions illustrated in the FIG. 11. In further exemplary embodiments of the present disclosure, the cooling applicator 411 can be larger or smaller in width or cross-sectional area as compared to the dimensions of the thermoelectric cooler 412.

The cooling applicator 411 can include a distal (contact) surface 14 that is configured to contact a skin surface. The distal surface 414 can be substantially flat. In further exemplary embodiments of the present disclosure, the distal surface 414 can be convex or concave to better match the local shape of skin tissue being treated and/or to provide good thermal contact with the skin surface when the apparatus 400 is placed on the area of the skin to be treated. In still further exemplary embodiments of the present disclosure, the cooling applicator 411 can be detachable from the thermoelectric cooler 412, e.g., so that a plurality of cooling applicator 411 having different sizes, shapes, and/or surface features as described herein can be used with a single thermoelectric cooler 412.

The distal contact surface 414 can have a large width or diameter configured to contact the surface of a region of skin, e.g., a diameter or width that is greater than about 3-10 cm, or greater than about 5 cm, to facilitate treatment of large areas of skin. In further embodiments, the width of the distal surface 414 can be small, e.g., on the order of 1-2 cm or less which may facilitate improved temperature control and/or treatment of particular features on the skin.

The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method of altering pigmentation in a skin of a patient, the method comprising:
    generating seed crystals on a contact surface of a cooling treatment probe;
    applying a coupling fluid to a treatment area on the skin of the patient; and
    applying the contact surface of the cooling treatment probe to the treatment area with the applied coupling fluid present, wherein the applying the contact surface of the cooling treatment probe to the treatment area with the applied coupling fluid present introduces an ice nucleating agent to the coupling fluid, the ice nucleating agent configured to promote ice formation in the coupling fluid and to limit supercooling of the skin in the treatment area, and wherein applying the contact surface of the cooling treatment probe to the treatment area with the applied coupling fluid present promotes ice crystal formation in the coupling fluid and wherein the ice crystal formation in the coupling fluid propagates into the skin of the patient.

2. The method of claim 1, wherein generating seed crystals on the contact surface of the cooling treatment probe comprises pre-cooling the contact surface of the cooling treatment probe to between −20° C. to 0° C. for a period of time before applying the contact surface of the cooling treatment probe to the treatment area with the applied coupling fluid present.

3. The method of claim 2, wherein the period of time comprises between 20 seconds and 2 minutes.

4. The method of claim 2, wherein pre-cooling the contact surface of the cooling treatment probe to between −20° C. to 0° C. comprises cooling the temperature of the contact surface of the cooling treatment probe to a temperature of approximately −10° C. for the period of time before applying the contact surface of the cooling treatment probe to the treatment area with the applied coupling fluid present.

5. The method of claim 2, wherein generating seed crystals on the contact surface of the cooling treatment probe further comprises applying water to the contact surface of the cooling treatment probe before applying the contact surface of the cooling treatment probe to the treatment area with the applied coupling fluid present.

6. The method of claim 5, wherein applying water to the contact surface of the cooling treatment probe comprises misting water onto the contact surface of the cooling treatment probe.

7. The method of claim 2, wherein the contact surface of the cooling treatment probe comprises an aluminum plate.

8. The method of claim 1, wherein the contact surface of the cooling treatment probe comprises a roughened surface comprising recessed areas configured to retain the seed crystals.

9. The method of claim 8, wherein the roughened surface is configured to promote formation of ice crystals from moisture in the air.

10. The method of claim 8, wherein the roughened surface comprises a knurled surface.

11. The method of claim 8, wherein the roughened surface has a roughness between 32-256 μin.

12. The method of claim 8, wherein the roughened surface has a roughness between 1000-2000 μm.

13. The method of claim 1, wherein the ice nucleating agent comprises the seed crystals.

14. The method of claim 1, wherein the coupling fluid comprises an aqueous fluid and a thickening agent to increase a viscosity of the aqueous fluid.

15. The method of claim 1, wherein applying the coupling fluid to the treatment area on the skin of the patient comprises applying a fluid carrier to the treatment area of the skin, the fluid carrier configured to retain the coupling fluid at the treatment area.

16. A method of altering pigmentation in a skin of a patient, the method comprising:
    applying a coupling fluid to a treatment area on the skin of the patient, the coupling fluid configured to limit supercooling of the skin, and the coupling fluid comprising a thickening agent increasing a viscosity of the coupling fluid to retain the coupling fluid at the treatment area; and
    applying a cooling treatment to the treatment area with the coupling fluid present, wherein applying the cooling treatment to the treatment area with the coupling fluid present promotes ice crystal formation in the coupling fluid and wherein the ice crystal formation in the coupling fluid propagates into the skin of the patient.

17. The method of claim 16, wherein the coupling fluid comprises an aqueous fluid.

18. The method of claim 17, wherein the coupling fluid freezes near 0 de. C.

19. The method of claim 16, further comprising abrading or piercing the treatment area prior to applying the cooling treatment.

20. The method of claim 16, wherein applying the cooling treatment comprises contacting a treatment surface of a cooling probe with the coupling fluid at the treatment area.

21. The method of claim 20, wherein the treatment surface of the cooling probe comprises a smooth surface.

22. The method of claim 20, wherein the treatment surface of the cooling probe comprises a textured surface.

\* \* \* \* \*